United States Patent [19]

Miller

[11] 4,151,842
[45] May 1, 1979

[54] BODY SPLINT/LITTER DEVICE

[76] Inventor: Larry C. Miller, 465 Oliveta Pl., La Canada, Calif. 91011

[21] Appl. No.: 883,387

[22] Filed: Mar. 6, 1978

Related U.S. Application Data

[63] Continuation of Ser. No. 733,250, Oct. 18, 1976, abandoned.

[51] Int. Cl.² .............................................. A61F 5/04
[52] U.S. Cl. .................................... 128/87 R; 5/82 B
[58] Field of Search .................. 128/78, 82 R, 87 R, 128/134; 269/81 R, 328, 322; 5/82 R, 82 B

[56] References Cited

U.S. PATENT DOCUMENTS

| | | | |
|---|---|---|---|
| 2,141,100 | 12/1938 | Warden | 5/82 |
| 3,469,268 | 9/1969 | Phillips | 128/87 |
| 3,609,778 | 10/1971 | Zeiner | 5/82 |
| 3,611,454 | 10/1971 | Klippel | 5/82 |
| 3,650,523 | 3/1972 | Darby | 128/134 |
| 3,719,187 | 3/1973 | Alansey | 128/87 X |
| 3,724,453 | 4/1973 | Dixon et al. | 128/87 |
| 3,732,863 | 5/1973 | Harrington | 5/82 X |
| 3,737,923 | 6/1973 | Prolo | 5/82 |
| 3,889,668 | 6/1975 | Ochs et al. | 128/134 |
| 3,933,154 | 1/1976 | Cabansag | 128/134 |

*Primary Examiner*—Lawrence W. Trapp
*Attorney, Agent, or Firm*—Arthur V. Doble

[57] ABSTRACT

A body splint/litter device for rapidly and securely immobilizing an injured person at an accident site prior to and while transporting the person to a medical facility for appropriate care and treatment. The body splint/litter includes a rigid substantially body-shaped panel of a size compatible with placement within a standard basket-type stretcher. The panel has a plurality of elongated slots at its side suitably spaced for purposes of handling the injured person. One end of each of several fastener straps is directly attached to the rigid panel by screws or other suitable fasteners. Additional slots are located along the edges of the panel at various locations through which the free ends of the several restraining straps may be passed and folded back over the edge of the panel for rapid securing and adjustment of each strap. A supplemental harness for restricting further motion of the head is also provided. Adjustable shoulder straps slidably mounted at one end of each such strap to a torso strap are provided to conveniently accommodate different body sizes.

17 Claims, 3 Drawing Figures

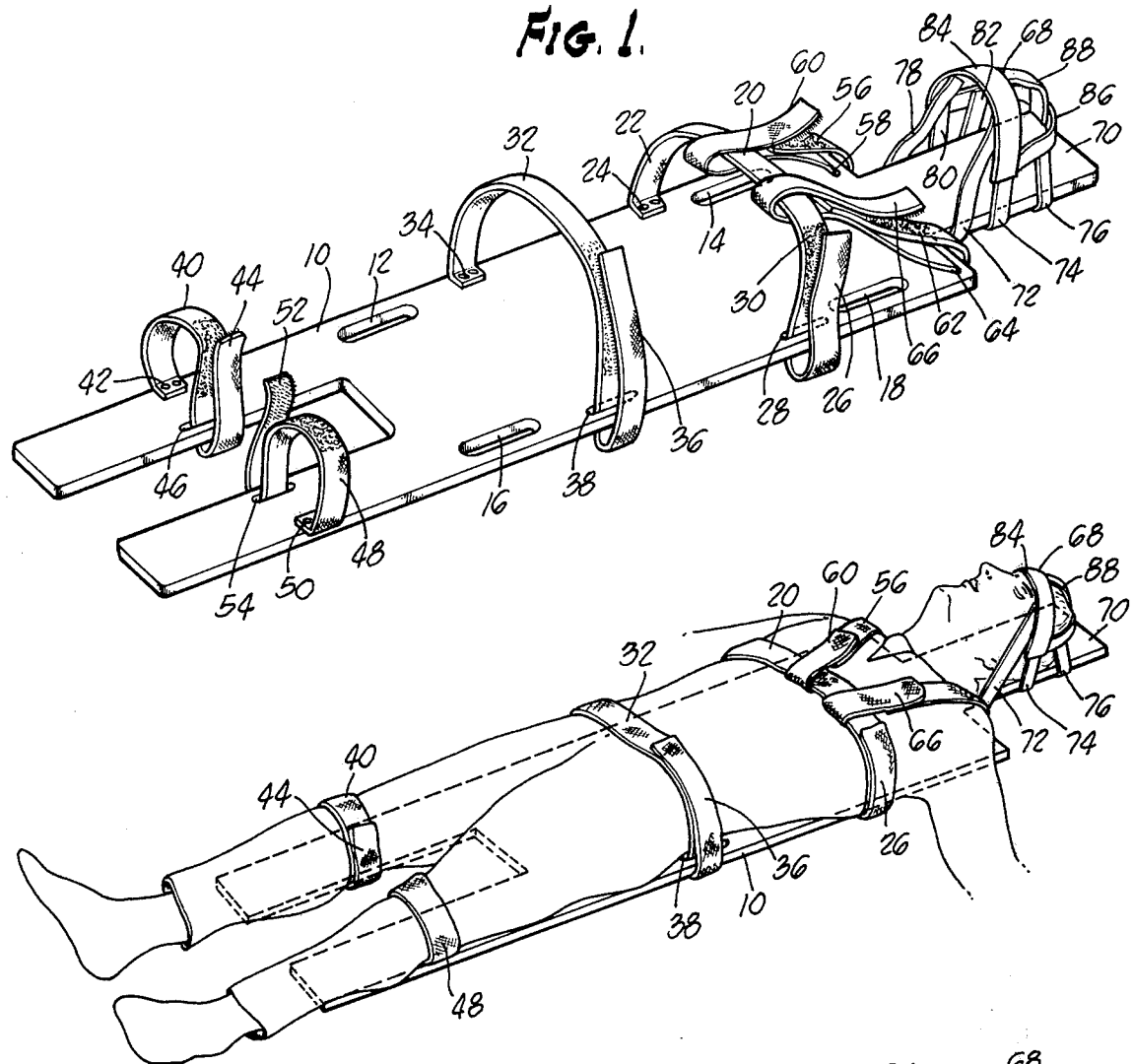
FIG. 1.
FIG. 2.
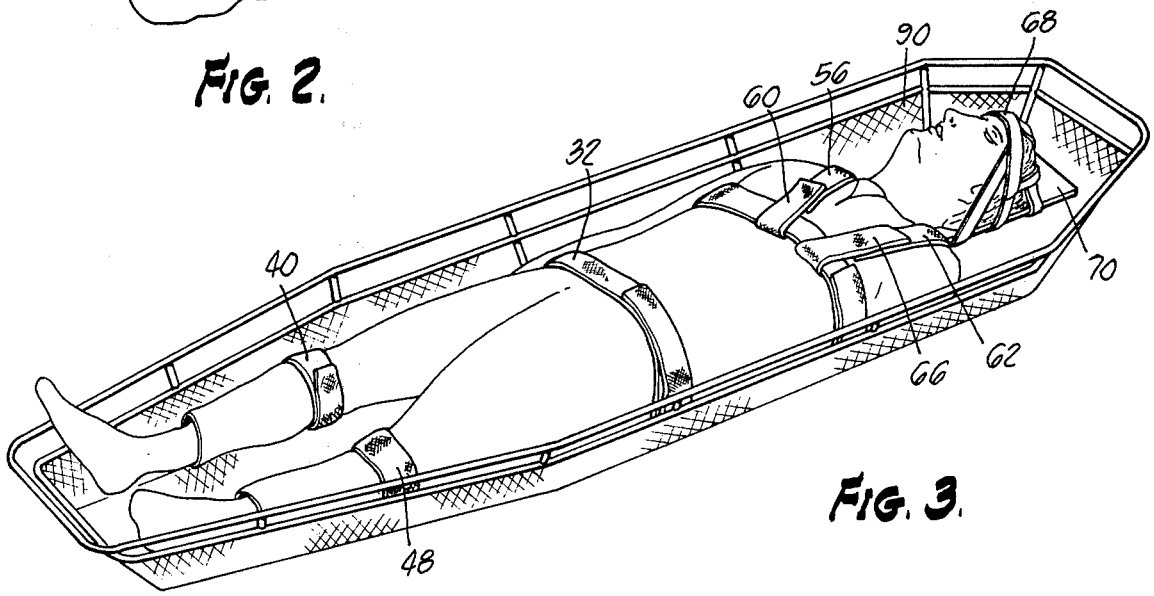
FIG. 3.

BODY SPLINT/LITTER DEVICE

This is a continuation, of abandoned application Ser. No. 733,250, filed on Oct. 18, 1976.

BACKGROUND OF THE INVENTION

1. Field of the Invention:

This invention relates to apparatus of the body splint/litter type for emergency handling of accident victims prior to and while being transported to an appropriate medical facility. It more particularly relates to a body splint/litter apparatus having a rigid support panel with a plurality of flexible, rapid-securing and easily-adjustable straps, and shoulder harnesses.

2. Description of the Prior Art:

Various forms of emergency body splint or litter types of apparatus have found extensive use by medical and rescue personnel over the years. Among the earliest, and perhaps the oldest in use, is a simple stretcher or body litter used by early man to move the ill or injured. It generally comprised either a rigid form made up of tree limbs, or was merely a large animal skin supported or suspended between two poles whereby the injured were transported by the process of dragging from place to place. As the arts of medicine and science progressed, so did the concepts of the mechanical handling of an injured person. It eventually became known in the field of emergency care that extreme caution was necessary in any attempted movement of an injured victim. Improper movement often resulted in further injury to the victim, the effects of which ranged from contributing to a prolonged recuperation period up to the level of causing irreparable damage to the injured party.

It was particularly determined that keeping the injured victim immobile during handling and movement to a medical facility was of paramount importance. Numerous devices for immobilizing an accident victim have been developed and used over the years. Most of them have been unsatisfactory because of limited flexibility of use and application, or clumsiness, or awkwardness in size, shape, weight, manner of securing the victim or adaptation of the device to a specific injury condition.

The following patents which represent the most pertinent art known to applicant clearly illustrate the novelty of applicant's invention:

| | | |
|---|---|---|
| 2,247,360 | 3,151,343 | 3,707,734 |
| 2,361,328 | 3,315,671 | 3,732,863 |
| 2,361,789 | 3,449,776 | 3,737,923 |
| 2,409,934 | 3,469,263 | 3,797,051 |
| 2,511,061 | 3,526,222 | 3,889,668 |
| 3,158,875 | 3,566,422 | |

Closer examination of these above inventions discloses the need for improved devices. These prior patents disclosed improvements in support systems and harness types, such as arrangements of webs and straps, or adjustable head restraints and cushions, folding support sections, partial supports, folding cots, bulky child-restrainers, collapsible telescoping or sliding sections, or simple stretchers with restraining straps, each of which offers some advantage or advantages, but none of which are ideally suitable for use with an accident victim having numerous injuries over the full span of his body. In particular, the upper-torso splint types, as shown in U.S. Pat. No. 3,969,268, are not suitable for use as a litter and provide only limited body protection and are used mainly for extracting a victim from wreckage and to subsequently aid in the placing of the victim in a litter for transportation. Regarding harness configurations, shoulder restraints as shown in U.S. Pat. No. 3,889,668, do not provide adequate flexibility of adjustment for different sized persons.

SUMMARY OF THE INVENTION

Applicant herein has conceived of an improved body splint/litter device for rapidly and securely immobilizing an injured person at an accident site prior to and while transporting the person from said site to a medical facility for appropriate care and treatment.

This improved device is basically a substantially full body-shaped rigid panel, having a plurality of elongated slots at its edges for handling the device by emergency personnel, in combination with flexible restraining straps and a head harness for restricting motion thereof.

One end of each of several flexible restraining fastener straps is directly attached to the rigid panel by screws or other suitable fasteners. Additional slots are located along the edges of the panel at various locations through which the free ends of the several restraining straps may be passed and folded back over the edge of the panel for rapid attachment and adjustment of each strap to itself.

The present invention shows several features of novelty over the prior art, including the general capability and objective of restraining the bone structure of nearly the entire body of an injured accident victim while concurrently serving as a fully independent litter.

It is an object of this invention to provide an improved body splint/litter combination in which a substantially body-shaped rigid panel is provided for supporting the body of an accident victim, including his head, neck, shoulders, upper and lower torso, and legs in a manner so as to restrain the body during transporting to a medical facility.

It is another object of the present invention to provide an improved body splint/litter which is suitable for use in combination with a standard basket-type stretcher of the type commonly used in rescue operations for supporting the body while being transported.

It is another object of this invention to provide a splint/litter combination device having flexible straps for supporting the full body of an accident victim, including a harness for restricting motion of the head of an accident victim during transporting to a medical facility.

It is a further object of this present invention to provide a body splint/litter device suitable for easy storage and transportation in a light-weight emergency automotive vehicle.

It is still a further object to provide a body splint/litter device that is economical to manufacture and use, as well as being durable, rugged, reliable and easy to operate and adjust.

For a better understanding of this present invention, together with other and further objects thereof, reference is made to the following description taken in connection with the accompanying drawings in which a preferred embodiment of the invention is illustrated, the scope of the invention being pointed out and contained in the appended claims.

BRIEF DESCRIPTION OF THE DRAWINGS

FIG. 1 is a perspective view of one embodiment of an improved body splint/litter combination device.

FIG. 2 is a perspective view of said body splint/litter combination device showing an accident victim in restrained position in the device and ready for transporting; and FIG. 3 is a perspective view of said body splint/litter combination device showing an accident victim in restrained position in the body splint/litter device and having been placed together in a standard basket-type rescue stretcher.

DESCRIPTION OF THE PREFERRED EMBODIMENTS

In FIG. 1 there is shown a preferred embodiment of this body splint/litter invention. At 10 there is shown a substantially full bodied-shaped rigid panel which serves as the main supporting portion of the device as a splint and as the principal support for the device as a litter. It is evident to one skilled in the art that rigid panel 10 may be constructed from any of several suitable materials and this invention shall not be limited thereby. Although wood is preferrable, metal, plastics or cellular-type materials are also usable. Ease of manufacture, expense and comfort to the victim are generally the controlling factors for material selection. Slots 12, 14, 16 and 18 serve as receptacles for the hands of the rescue team and litter bearers. A plurality of flexible straps are used to secure an accident victim to panel 10 in order to immobilize all portions of the victim's body while being moved from an accident site to a medical facility. Strap 20 is used to secure the upper torso, i.e., in the area of the person's chest, to panel 10. One end 22 of strap 20 is attached to panel 10 at a point 24 by any suitable fastener such as one or more woodscrews. The opposite end 26 of strap 20, once placed over the person's chest, passes through a thin slot 28 which is one of several thin slots located at the edges of panel 10 to receive the ends of the various straps. Once passing through slot 28, the end 26 is pulled snugly by emergency personnel and is folded back over the outer edge of panel 10 for cohesive contact with the outer surface 30 of strap 20 at any of an infinite positions of adjustments.

The method for accomplishing such infinite adjustment may be achieved by any one of several commonly used means which, of themselves, do not constitute invention herein. For example, friction-gripping devices buckles, or the use of loop and hook fasteners may be employed.

Once having secured the person's upper chest to panel 10 by strap 20, strap 32 may be used to secure the lower torso of the victim to panel 10. Strap 32 is connected to panel 10 at point 34 through the use of any suitable fastener. End 36 of strap 32 is passed through thin slot 38 and is folded back over panel 10 for gripping contact with the central portion of strap 32 and may be easily adjusted to any convenient position as described above with respect to the operation and adjustment of strap 20.

Likewise, strap 40 may be used to secure a person's right leg to leg segment of panel 10. Strap 40 is securely fastened to panel 10 by any suitable fastener at point 42. The free end 44 of strap 40 passes over the person's leg and through thin slot 46 and is folded back over an edge of panel 10 for gripping contact with the central portion of strap 40 and may be readily adjusted in the same manner as strap 20 as previously described above. Strap 48 may be used to secure a person's left leg to leg segment of panel 10. Strap 48 is securely fastened to panel 10 by any suitable fastener at point 50. The free end 52 of strap 48 passes over the person's left leg and through thin slot 54 and is folded back over an edge of panel 10 for gripping contact with the central portion of strap 48 and may be readily adjusted in the same manner as strap 20, as previously described above. The leg segments of panel 10 are nondivergent to maintain a minimal profile for ease of handling.

Right shoulder strap 56 is loosely threaded through panel 10 through slot 58. Free end 60 of strap 56 passes over the person's right shoulder and chest; passes under strap 20; and is folded back over strap 20 for gripping contact only with the central portion of strap 56, part of the folded-over portion of strap 56 being in slideable contact with strap 22 for ease of adjustment with regard to varying sizes of accident victims who may be placed in this device.

Left shoulder strap 62 may likewise be used to secure a person's left shoulder to panel 10. Strap 62 is threaded through panel 10 at slot 64. Free end 66 of strap 62 passes over the person's right shoulder and his chest; passes under strap 20; and is also folded back over strap 20 and secured and adjusted in the same fashion as strap 56.

A multi-strapped head harness 68 is attached to segment 70 of panel 10 by head-harness straps 72, 74 and 76, which are positioned alongside the left side of the victim's head, when in the device, and by head-harness straps 78, 80 and 82 positioned alongside the right side of the victim's head. Strap 84 is used in a restraining position across the victim's forehead, while strap 86 is positioned across the top of the victim's head. A transverse strap 88 is used between straps 84 and 86 to maintain relative positioning therebetween. Head-harness straps 72, 74, 76, 78, 80 and 82 may be of any flexible material suitable for restraining purposes and may be attached to panel 10 by any suitable fastening means. Head harness 68 restrains the motion of the victim's head in all directions including longitudinal, transverse and lateral.

FIG. 2 best demonstrates the utility of the subject invention with an accident victim positioned and secured onto the device. Head-harness 68 is in place on the victim's head, with chest strap 20, lower torso strap 32, leg straps 40 and 48, securely fastened and immobilizing the victim's body.

FIG. 3 is offered for further clarification regarding the adaptability of the subject invention for convenient use with a standard basket-type litter as shown at 90.

What I claim as new is:

1. In a combined body splint/litter device for use in emergency immobilization and transportion of an accident victim to a medical facility, an improvement comprising:
   (a) a substantially full body shaped rigid panel having a central torso section, two nondiverging leg segments appended to the lower part of said torso section and a head and neck section narrower in width than the torso section appended to the upper part of said torso section, for transportably supporting the full body of an accident victim;
   (b) strap means connected to said splint means for securing the body of the accident victim to said splint means; and (c) a head-harness cooperatively associated with said splint means for restraining in all directions the motion of the accident victim's head when the victim is positioned on said splint means, whereby said device may be employed as a body splint and as a litter for securing, immobilizing and moving an accident victim.

2. In a combined body splint/litter device for use in emergency mobilization and transportation of an accident victim to a medical facility, an improvement comprising:
(a) a substantially full body-shaped rigid panel having a central torso section, two nondiverging leg segments appended to the lower part of the torso section and a head and neck section narrower in width than the torso section appended to the upper part of the torso section, for transportably supporting the full body of an accident victim; and
(b) strap means connected to said panel for securing the body of the accident victim to said panel, whereby said device may be employed as a body splint and as a litter for securing, immobilizing and moving an accident victim.

3. In the device described in claim 2, above, said panel having gripping means adapted for easy gripping by emergency personnel, said gripping means comprising a plurality of handles, defined by elongated slots formed proximate the edges of the panel to accommodate the hands of emergency personnel when carrying the device.

4. In the device described in claim 2, above, the panel being of a size compatible for storage in a light-weight emergency rescue automotive vehicle.

5. In the device described in claim 2, above, in which the panel is of a size compatible for cooperative use with and placement into another litter of the basket-type for transportation to a medical facility.

6. The body-splint/litter device described in claim 2, above, wherein said strap means comprises a plurality of flexible straps attached to said panel, said straps being adapted to partially cover, adjustably restrain, and immobilize the body of an accident victim.

7. In the device described in claim 6, above, said panel having means adaptable for adjustable attachment of said flexible straps to said panel for restraint and immobilization of said victim, said means comprising a plurality of panel segments having thin slots located proximate the edges thereof.

8. The body splint/liter device described in claim 6, above, wherein the flexible straps comprise a chest strap, a lower torso strap, leg straps, and a plurality of shoulder straps mounted in slideable cooperation with said chest strap for adjustment and releasable securing the body of an accident victim to the rigid panel.

9. The body splint/litter device as described in claim 6, above, wherein said means for securing the body of an accident victim to the rigid panel comprises fastener straps in cooperative association with the panel, the straps each having one side thereof fastenable to another side of itself for rapidly and adjustably securing and immobilizing the body of an accident victim for protection while being transported to a medical facility.

10. In the device described in claim 1, above, said panel having gripping means adapted for easy gripping by emergency personnel, said gripping means comprising a plurality of handles, defined by elongated slots formed proximate the edges of the panel to accommodate the hands of emergency personnel when carrying the device.

11. In the device described in claim 1, above, the panel being of a size compatible for storage in a light-weight emergency rescue automotive vehicle.

12. In the device described in claim 1, above, in which the panel is of a size compatible for cooperative use with and placement into another liter of the basket-type for transportation to a medical facility.

13. The body-splint/litter device described in claim 1, above, wherein said strap means comprises a plurality of flexible straps attached to said panel, said straps being adapted to partially cover, adjustably restrain and immobilize the body of an accident victim longitudinally, transversely and laterally.

14. In the device described in claim 13, said panel having means adapted for adjustable attachment of said flexible straps at one end of each strap to said panel for restraint and immobilization of said accident victim, said means comprising a plurality of panel segments having their slots located proximate to the edges thereof.

15. The body splint/litter device described in claim 13, above, wherein the flexible straps comprise a chest strap, a lower torso strap, leg straps, and a plurality of shoulder straps mounted in slideable cooperation with said chest strap for adjustment and releasably securing the body of an accident victim to the rigid panel.

16. The body splint/litter device as described in claim 13, above, wherein said means for securing the body of an accident victim to the rigid panel comprises fastener straps in cooperative association with the panel, the straps each having one side thereof fastenable to another side of itself for rapidly and adjustably securing and immobilizing the body of an accident victim for protection while being transported to a medical facility.

17. In a combined body splint/litter device for use in emergency immobilization and transportation of an accident victim to a medical facility, an improvement comprising:
(a) a substantially full body-shaped rigid panel for transportably supporting the body of an accident victim, a substantially full-body shaped rigid panel having a central torso section, two nondiverging leg segments appended to the lower part of said torso section and a head and neck section narrower in width than the torso section appended to the upper part of said torso section, for transportably supporting the full body of an accident victim, the panel having a plurality of thin slots located near the edges of the panel formed by elongated slots and the outer segments of the panel;
(b) a plurality of flexible fastener straps, in cooperative association with the rigid panel, adapted to rapidly cover, adjustably restrain, and immobilize the upper and lower torso and legs of an accident victim; and
(c) a head harness in cooperative association with the panel, the head harness having a forward strap, a strap across the top of the head, a transverse strap joining the forward strap and the strap at the top of the head at their respective approximate centers, the head harness further having a plurality of straps on each side to secure the aforesaid straps to said panel.

* * * * *